(12) United States Patent
Rosenberg et al.

(10) Patent No.: US 8,815,999 B2
(45) Date of Patent: *Aug. 26, 2014

(54) CROSS-LINKER

(75) Inventors: Jan-Erik Rosenberg, Falkenberg (SE); Daniel Röme, Lund (SE); David Persson, Malmö (SE); Erik Lager, Lund (SE); Malin Knutsson, Ystad (SE); Dane Momcilovic, Lund (SE)

(73) Assignee: Nexam Chemical AB, Lund (SE)

( * ) Notice: Subject to any disclaimer, the term of this patent is extended or adjusted under 35 U.S.C. 154(b) by 43 days.

This patent is subject to a terminal disclaimer.

(21) Appl. No.: 13/641,470

(22) PCT Filed: Apr. 15, 2011

(86) PCT No.: PCT/EP2011/055992
§ 371 (c)(1),
(2), (4) Date: Dec. 20, 2012

(87) PCT Pub. No.: WO2011/128431
PCT Pub. Date: Oct. 20, 2011

(65) Prior Publication Data
US 2013/0096256 A1    Apr. 18, 2013

(30) Foreign Application Priority Data

Apr. 16, 2010 (EP) .................. 10160198
Dec. 6, 2010 (EP) .................. 10193811

(51) Int. Cl.
| C08G 63/60 | (2006.01) |
| C08G 73/10 | (2006.01) |
| C07D 209/48 | (2006.01) |
| C08L 79/08 | (2006.01) |
| C07C 65/38 | (2006.01) |
| C07D 307/89 | (2006.01) |

(52) U.S. Cl.
CPC ........ C08G 73/1085 (2013.01); C08G 73/1014 (2013.01); C07D 209/48 (2013.01); C08L 79/08 (2013.01); C08G 73/1071 (2013.01); C07C 65/38 (2013.01); C07D 307/89 (2013.01); C08G 73/1067 (2013.01); C08G 73/1039 (2013.01)
USPC ........... 524/599; 549/245; 549/244; 549/429; 524/600

(58) Field of Classification Search
None
See application file for complete search history.

(56) References Cited

U.S. PATENT DOCUMENTS

| 5,567,800 | A |   | 10/1996 | Hergenrother et al. |
| 5,681,967 | A |   | 10/1997 | Hergenrother et al. |
| 5,817,774 | A | * | 10/1998 | Delecki et al. .................. 534/10 |
| 6,136,949 | A | * | 10/2000 | Earls et al. ..................... 528/353 |
| 6,344,523 | B1 |  | 2/2002 | Hawthorne et al. |
| 2013/0079479 | A1 | * | 3/2013 | Rosenberg et al. ........... 526/193 |

OTHER PUBLICATIONS

Solid State Technology, New Tech Enables Polyimide Crosslink Temp Control, Oct. 4, 2010, pp. 1-4.*
International Search Report for corresponding International Application No. PCT/EP2011/055992 mailed Jun. 24, 2011.
Hergenrother, "Acetylene-Terminated Imide Oligomers and Polymers Therefrom", Polymer Preprints, American Chemical Society, vol. 21 (1), 1980, pp. 81-83 (cited in specification on p. 2).

* cited by examiner

*Primary Examiner* — Susannah Chung
*Assistant Examiner* — Robert T Butcher
(74) *Attorney, Agent, or Firm* — Renner, Otto, Boisselle & Sklar, LLP

(57) ABSTRACT

Disclosed are novel cross-linkable end-cappers for oligo- and polyimides. End-capped oligo- and polyimides comprising such an end-capper may be cured at a lower temperature compared to oligo- and polyimides end-capped with PEPA.

20 Claims, 4 Drawing Sheets

CROSS-LINKER

This application is a national phase of International Application No. PCT/EP2011/055992 filed Apr. 15, 2011 and published in the English language, which claims priority to Application No. EP 10160198.7 filed Apr. 16, 2010 and Application No. EP 10193811.6 filed Dec. 6, 2010.

FIELD OF THE INVENTION

The present invention refers to novel cross-linkable end-cappers for oligo- and polyimides, which end-cappers comprise carbon-carbon triple bonds. Further, the present invention refers to compounds comprising a residue of such novel cross-linkable end-cappers, such as an end-capped oligo- or polyimide. It also relates to an article comprising the oligo- or polyimide, wherein the oligo- or polyimide optionally has been cross-linked by heating it.

BACKGROUND

Polymers has for long been used as replacement material for other materials, such as metals. They have the advantage of being light-weight material, which are relative easy to shape. However, polymers do typically have lower mechanical strength compared to metals. Further, they are less heat resistant.

The need for resistant polymers led to the development of aromatic polyimides. Polyimides are polymers comprising imide bonds. Aromatic polyimides are typically synthesized by condensation of aromatic carboxylic acid dianhydride monomers, such as pyromellitic dianhydride, 4,4'-oxydiphthalic anhydride, 2,2-bis-[4-(3,4-dicarboxyphenoxy)phenyl]-propane dianhydride, 3,3',4,4'-benzophenonetetracarboxylic acid dianhydride or 3,3',4,4'-tetracarboxybiphenyl dianhydride, with aromatic diamine monomers, such as 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline or 3,4'-oxydianiline.

Polyimides obtained via condensation of pyromellitic dianhydride and 4,4'-oxydianiline are among others sold under the trademarks Vespel® and Meldin®. They are materials which are lightweight and flexible, and which have good resistant to heat and chemicals.

Further, thermoset polyimides have inherent good properties, such as wear and friction properties, good electrical properties, radiation resistance, good cryogenic temperature stability and good flame retardant properties. Therefore, they are used in the electronics industry for flexible cables, as an insulating film on magnet wire and for medical tubing. Polyimide materials are also used in high or low temperature exposed applications as structural parts were the good temperature properties is a prerequisite for the function.

The need to improve the processability, while keeping the mechanical properties, of polyimides for use in airplanes and aerospace applications led to the introduction of cross-linking technologies. As the polymer chains are cross-linked, they may be shorter whilst the mechanical properties are maintained or even improved. Shorter polymer chains have the advantage of being easier to process, as the viscosity of the polymer melt is lower.

Examples of such cross-linking technologies include the bismaleimides and the nadimide-based PMR resins, which undergo cure at temperatures near 250° C. However, such thermoset polyimides will not withstand oxidative degradation on long-term exposure at temperatures above 200° C., as the crosslinking moieties have inferior thermal stability, compared to the oligoimide units.

In attempts to improve the thermal stability, thermoset polyimides containing phenylethynyl-substituted aromatic species as the reactive moieties have been developed.

U.S. Pat. No. 5,567,800 discloses phenylethynyl terminated imide oligomers (PETIs). Such oligomers may be prepared by first preparing amino terminated amic acid oligomers from dianhydride(s) and an excess of diamine(s) and subsequently end-cap the resulting amino terminated amic acid oligomers with phenylethynyl phtalic anhydride (PEPA). The amic acid oligomers are subsequently dehydrated to the corresponding imide oligomers.

Upon heating the triple bonds will react and cross-link the end-capped polyimid, thereby further improving its heat resistance and mechanical strength. As disclosed by U.S. Pat. No. 5,567,800 heating to at least 350° C. is necessary to cure the PETI.

However, for some applications the high curing temperature may be considered a problem. For instance, the properties (such as the coefficient of thermal expansion) of flexible polyimide films, having a melting temperature below 350° C., may be improved via cross-linking. However, the high temperature (above 350° C.) needed to initiate cross-linking will make the processing impossible.

If the curing temperature may be lowered, a film may be formed from a solution. During the drying step, curing may then be initiated by heating the film without melting it.

As an alternative to PEPA, also ethynyl phtalic anhydride (EPA) has been used as cross-linker in polyimides (Hergenrother, P. M., "Acetylene-terminated Imide Oligomers and Polymers Therefrom", Polymer Preprints, Am. Chem. Soc., Vol. 21 (1), p. 81-83, 1980). Although polyimides comprising EPA may be cross-linked at a somewhat lower temperature, i.e. at about 250° C., it suffers from other drawbacks. The exchange of the phenyl ethynyl group to an ethynyl group implies that other reaction pathways than the desired curing mechanism, such as chain extension, are favored. As a consequence, EPA has not found any wide use as a replacement to PEPA as a low temperature curing end-capper. Further, the manufacture of EPA requires protective group chemistry hampering its commercial potential.

U.S. Pat. No. 6,344,523 addresses the disadvantageous of the high curing temperature discussed above and discloses that use of sulfur or organic sulfur derivatives as curing promoters may lower the curing temperature of PETI. However, the introduction of such promotors suffers from other disadvantages. In particular the curing results in chain extension rather than cross-linking as two ethynyl groups react along with one sulfur radical ultimately forming a thiophene structure.

Thus, there is need within the art for an alternative cross-linking monomer, overcoming the above-mentioned deficiencies, to replace PEPA and EPA in poly- and oligoimides.

SUMMARY

Consequently, the present invention seeks to mitigate, alleviate, eliminate or circumvent one or more of the above-identified deficiencies in the art and disadvantages singly or in any combination by providing a compound according to formula (I) or (II)

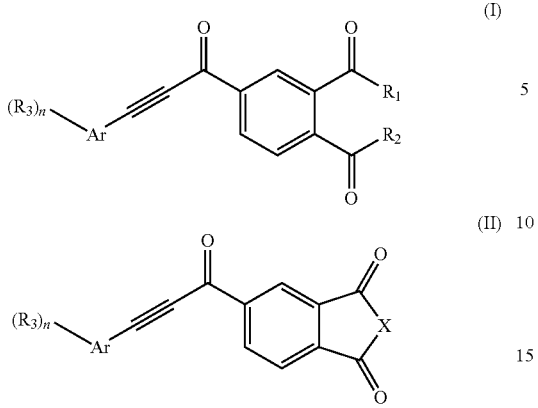

wherein

"Ar" is an aryl or a heteroaryl;

R1 and R2 are independently selected from the group consisting of OH, halo, OC1-C8 alkyl, NH2, NHC1-8 alkyl, N(C1-8 alkyl)$_2$, wherein said alkyl may be the same or different, OC(O)C1-8 alkyl, OC0-1 alkylenephenyl, and NHC0-1 alkylenephenyl;

R3 is, independently if "n" is 2 or more, selected from the group consisting of C1-4 alkyl, OC1-4 alkyl, halogen, cyano, nitro, C1-4 fluoroalkyl;

the substituent(s) R3 may be connected to any substitutable atom(s) of "Ar";

"n" is an integer from 0 (zero) to 5; and

"X" is selected from the group consisting of O (oxygen), NH, N-phenyl, N-benzyl, and N—C1-8 alkyl. A preferred example of such a compound is 5-(3-phenylprop-2-ynoyl) isobenzofuran-1,3-dione.

Another aspect of the invention relates to an oligo- or polyimide comprising a residue according to formula (III),

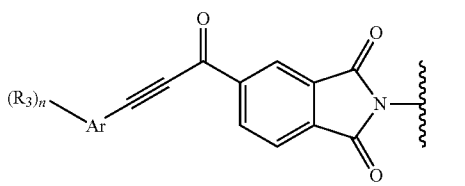

wherein the waved line indicates the point of attachment to the oligo- or polyimide;

"Ar" is an aryl or a heteroaryl;

R3 is, independently if "n" is 2 or more, selected from the group consisting of C1-4 alkyl, OC1-4 alkyl, halogen, cyano, nitro, C1-4 fluoroalkyl;

the substituent(s) R3 may be connected to any substitutable atom(s) of "Ar"; and "n" is an integer from 0 (zero) to 5. Typically, such an oligo- or polyimide comprises at least one residue of an aromatic dianhydride selected from the group consisting of pyromellitic dianhydride, 4,4'-oxydiphthalic anhydride, 2,2-bis-[4-(3,4-dicarboxyphenoxy)phenyl]-propane dianhydride, 3,3', 4,4'-benzophenonetetracarboxylic acid dianhydride, 3,3',4, 4'-tetracarboxybiphenyl dianhydride, 4,4',5,5'-sulfonyldiphthalic anhydride, and 5,5'-(perfluoropropane-2, 2-diyl)bis(isobenzofuran-1,3-dione) and at least one residue of an aromatic diamine selected from the group consisting of 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline, and 3,4'-oxydianiline. The oligo- or polyimide may further have a number average molecular weight of about 1,000 to 20,000, such as from about 2,500 to 10,000. Further, the oligo- or polyimide may comprise one or two residue(s) according to formula (III), 1 to 19, 20 to 200, or more than 200 residues of said aromatic diamine and the aromatic dianhydride, respectively.

Another aspect of the invention relates to composition comprising such an oligo- or polyimide. Such a composition may comprise an additional polymer, and/or at least one filler, reinforcement, pigment, and/or plasticizer. Typically, the composition comprises at least 10 wt % of the oligo- or polyimide.

Another aspect of the invention relates to use of a compound according to formula (I) or (II), to harden an epoxy resin. Further, an aspect of the invention relates to a hardened epoxy resin obtainable by hardening of an epoxy resin with a compound according to formula (I) or (II). In addition, an aspect of the invention relates to a method of hardening epoxy resin. Such a method comprises the step of mixing a compound according to formula (I) or (II) with the epoxy resin. Subsequently, the resulting mixture may be heated.

Another aspect of the invention relates to article comprising an oligo- or polyimide, or an epoxy resin, comprising a residue of a compound according to formula (I) or (II). The oligo- or polyimide, or the epoxy resin, has preferably been cured by heating it.

Another aspect of the invention relates to method of producing a compound according to formula (II) as disclosed above, wherein "X" is O (oxygen). Such a method comprises the step of:

reacting trimellitic anhydride chloride with a compound according to formula (IV)

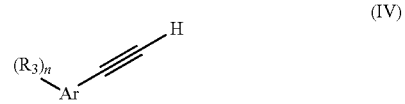

wherein

"Ar" is an aryl or a heteroaryl;

R3 is, independently if "n" is 2 or more, selected from the group consisting of C1-4 alkyl, OC1-4 alkyl, halogen, cyano, nitro, C1-4 fluoroalkyl;

the substituent(s) R3 may be connected to any substitutable atom(s) of "Ar"; and "n" is an integer from 0 (zero) to 5. The reaction between trimelletic anhydride and the compound according to formula (IV) may be performed in the presence of a compound comprising palladium and a compound comprising cupper.

Another aspect of the invention relates to an oligo- or polyimide obtainable by co-polymerization of a compound according to formula (I) or (II), an aromatic dianhydride, and an aromatic diamine.

Another aspect of the invention relates to a compound according to formula (XV) or (XVI)

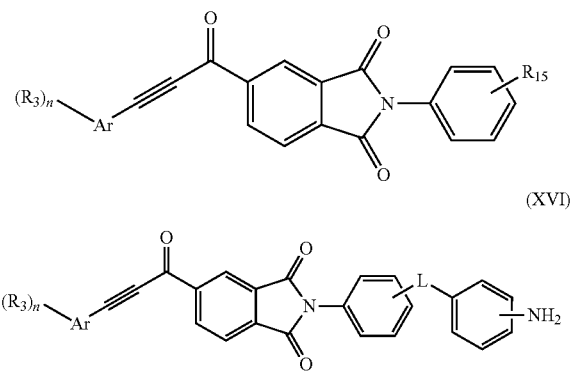
(XV)

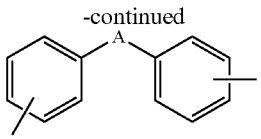

(XVI)

wherein
"Ar" is an aryl or a heteroaryl;
"n" is an integer from 0 (zero) to 5;
R3 is, independently if "n" is 2 or more, selected from the group consisting of C1-4 alkyl, OC1-4 alkyl, halogen, cyano, nitro, C1-4 fluoroalkyl;
R15 is OH, NH2, COOH, C(O)OC1-8 alkyl, or C(O)C1, and is connected to any substitutable carbon atom of the indicated benzene residue of formula (XV);
"L" is a direct bond or a moiety selected from the group consisting of —O—, —S—, —C(O)—, —C(CH₃)₂—, —C(CF₃)₂—, —CH₂—, 3-oxyphenoxy group, 4-oxyphenoxy group, 4'-oxy-4-biphenoxy group, and 4-[1-(4-oxyphenyl)-1-methylethyl]phenoxy group; and
"L" and the NH2 group of formula (XVI), respectively, are connected to any substitutable carbon atoms of the respective indicated benzene residue of formula (XVI).

Another aspect of the invention relates to a derivative according to formula (IIIb)

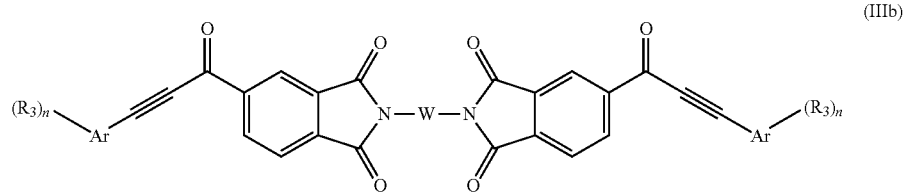
(IIIb)

wherein

"Ar" is an aryl or a heteroaryl;

"n" is an integer from 0 (zero) to 5;

R3 is, independently if "n" is 2 or more, selected from the group consisting of C1-4 alkyl, OC1-4 alkyl, halogen, cyano, nitro, C1-4 fluoroalkyl; and "W" is a radical selected from the group consisting of:

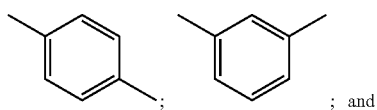
; and wherein "A" is a direct bond or a moiety selected from the group consisting of —O—, —S—, —C(O)—, —C(CH₃)2-, —C(CF₃)₂—, —CH₂—, 3-oxyphenoxy group, 4-oxyphenoxy group, 4'-oxy-4-biphenoxy group, and 4-[1-(4-oxyphenyl)-1-methylethyl]phenoxy group.

Another aspect of the invention relates to a composition comprising a derivative according to formula (IIIb), and an oligo- or polyimide comprising a residue of a compound according to formula (I) or (II), and/or a non-acetylenical oligo- or polyimide.

Further advantageous features of the invention are defined in the dependent claims. In addition, advantageous features of the invention are elaborated in embodiments disclosed herein.

DETAILED SUMMARY OF PREFERRED EMBODIMENTS

Definitions

In the context of the present application and invention, the following definitions apply:

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)₂" is equivalent to "NH2" (amino).

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" "C1-6 alkylene" denotes alkylenyl or alkylene having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(C0 alkylene)NH₂" is equivalent to "NHNH₂" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H₂N(C2 alkylene)NH₂", "H₂N(C3 alkylene)NH₂", "N(C4 alkylene)", "N(C5 alkylene)" and "N(C2 alkylene)₂NH" is equivalent to 1,2-diamino ethane, 1,3-diamino propane, pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "fluoroalkyl" and "fluoroalkylene", used alone or as a suffix or prefix, refers to groups in which one, two, or three of the hydrogen(s) attached to any of the carbons of the corresponding alkyl- and alkylene-groups are replaced by fluoro.

Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

As used herein, the term "aryl" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, and/or aryls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl groups include monocyclic and bicyclic (e.g., having 2 fused rings) systems.

As used herein, the term "substitutable" refers to an atom to which a hydrogen may be covalently attached, and to which another substituent may be present instead of the hydrogen. A non-limiting example of substitutable atoms includes the carbon-atoms of pyridine. The nitrogen-atom of pyridine is not substitutable according to this definition.

Embodiments

It has unexpectedly been revealed that compounds according to formula (I) or (II),

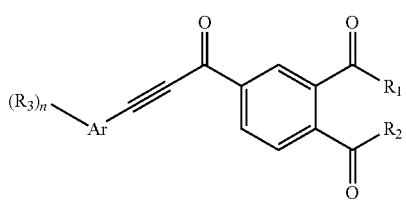

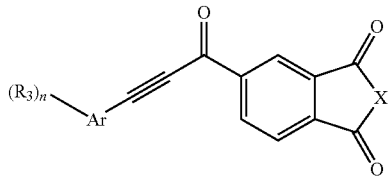

wherein

"Ar" is an aryl, such as phenyl or naphtyl, or a heteroaryl, such as thiophenyl or furanyl;

R1 and R2 are independently selected from the group consisting of OH, halo, such as chloro, OC1-C8 alkyl, such as OC1-C4 alkyl, NH2, NHC1-8 alkyl, N(C1-8 alkyl)₂, wherein said alkyl may be the same or different, OC(O)C1-8 alkyl, OC0-1 alkylenephenyl, and NHC0-1 alkylenephenyl;

R3 is, independently if "n" is 2 or more, selected from the group consisting of C1-4 alkyl, such as methyl, OC1-4 alkyl, such as methoxy, halogen, cyano, nitro, C1-4 fluoroalkyl, such as trifluoromethyl;

the substituent(s) R3 may be connected to any substitutable atom(s) of "Ar";

"n" is an integer from 0 (zero) to 5;

"Ar" is unsubstituted if "n" is 0 (zero); and

"X" is selected from the group consisting of O (oxygen), NH, N-phenyl, N-benzyl, and N—C1-8 alkyl;

may be used as end-cappers for oligo- and polyimides to obtain end-capped oligo- and polyimides that may be cross-linked at significantly lower temperatures compared to PETI.

Thus, an embodiment relates to a compound according to formula (I) or (II) as disclosed herein.

Typically, oligo- and polyimides comprising residues of compounds according to formula (I) or (II) may be cross-linked (cured) well below 300° C., such as at about 250° C. Thus, such oligo- and polyimides may be cross-linked at temperatures wherein also oligo- and polyimides comprising EPA are cross-linked.

However, in contrast to EPA, compounds according to formula (I) or (II) has no hydrogen atom directly attached to the carbon-carbon triple bond (acetylenic hydrogen). As a consequence, compared to EPA, cross-linking is more favored for compounds according to formula (I) or (II) as non-oxidative head-to-head coupling (Straus coupling) is not possible for such compounds. In addition, the synthesis of compounds according to formula (I) or (II) are not dependent on protective group chemistry decreasing the complexity of their manufacture compared to EPA.

It has further been found that compounds according to formula (I) or (II) are soluble in a more diverse variety of solvents compared to PEPA. As an example, it has been found that 5-(3-phenylprop-2-ynoyl)isobenzofuran-1,3-dione is soluble at least in cresol, dimethylacetamide (DMAc), dimethylformamide (DMF), dimethylsulfoxide (DMSO), methylethylketone (MEK) at elevated temperatures (eg. 75° C.), N-Methyl-2-pyrrolidone (NMP), and tetrahydrofuran (THF).

The preparation of compounds according to formula (I) or (II) are generally based on readily available raw materials, such as trimellitic anhydride and ethynylaryls, such as ethynylbensen.

Typically, trimelletic anhydride is activated by reaction with thionyl chloride to form an acid chloride, which is coupled to an ethynylaryl in a palladium catalyzed reaction.

According to an embodiment "Ar" in formula (I) and (II) is an aryl, such as phenyl or napthyl. Preferably, "Ar" is phenyl. "Ar" may also be a functional equivalent to phenyl, such as thiophenyl.

If "Ar" is phenyl, then compounds according to formula (I) or (II) may be represented by formula (Ia) or (IIa), respectively,

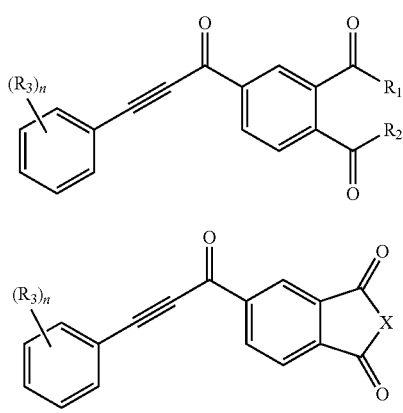

wherein R1, R2, R3 and "X" have the meaning indicted above for formula (I) and (II). In formula (Ia) and (IIa), R3 may connected to any of the substitutable carbon atoms in the phenyl group.

The integer "n" is preferably 0 (zero) or 1, such as being 0 (zero). If "n" is 1 or more, R3 is preferably, independently if "n" is 2 or more, selected from the group consisting of methyl, methoxy, nitro, and trifluoromethyl. As "n" may be 0 (zero), "Ar" may be un-substituted.

According to one embodiment "n" is 0 (zero) and "Ar" is phenyl.

Although the compound used in the manufacture of end-capped oligo- and polyimided may be a compound according to formula (I), the compound initially synthesized is typically a compound according to formula (II). In a compound according to formula (II), "X" is preferably O (oxygen), NH or NMe, such as being O (oxygen). As readily understood by the skilled artisan, compounds according to formula (II) may readily be converted into compounds according to formula (I), such as by reaction with mono-hydric alcohols.

According to one embodiment, compounds to be used as end-cappers are synthesized as compounds according to formula (II). These compounds may then be converted into compounds according to formula (I) prior to being used as end-cappers. In such compounds, R1 and R2 are preferably selected from OH, chloro, and OC1-C8 alkyl, such as methyl or ethyl. Preferably, R1 and R2 represent the same type of substituent.

In addition to what haven been described above, R1 and R2 may also represent a group activated for coupling with amines, eg. an activated ester group. Coupling of carboxy groups and amino groups to create amides is a common reaction and various ways of activating the carboxy group for such coupling have been described within the art. As an example, in Tetrahedron 2004, 60, 2447-2467, various coupling agent for peptide coupling, i.e. coupling of carboxy groups and amino groups, in organic synthesis has been reviewed. In an embodiment wherein "Ar" is phenyl and "n" is one, the substituent may be in para-position ("Ar" thus representing 1,4-substituted benzene). Having a substituent in 2-position (orto), may increase the curing temperature and this may, dependent on the circumstances, be advantageous or disadvantageous.

In a preferred embodiment, the compound according to formula (I) or (II) is 5-(3-phenylprop-2-ynoyl)isobenzofuran-1,3-dione, also denoted PETA (PhenylEthynylTrimelleticAnhydride). PETA has the structure indicated below.

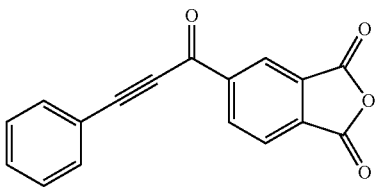 [SMILES: O=C(C#Cc1ccccc1)c1ccc2c(c1)C(=O)OC2=O]

In addition to compounds according to formula (I) and (II), a further embodiment relates to compounds according to formula (V) and (VI)

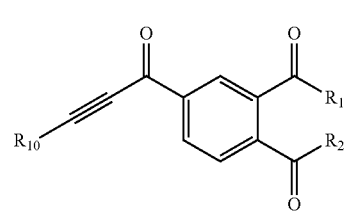

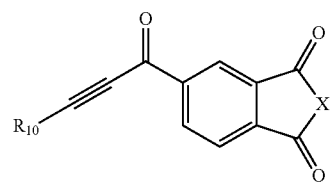

wherein

R1 and R2 are independently selected from the group consisting of OH, halo, such as chloro, OC1-C8 alkyl, such as OC1-C4 alkyl, NH2, NHC1-8 alkyl, N(C1-8 alkyl)$_2$, wherein said alkyl may be the same or different, OC(O)C1-8 alkyl, OC0-1 alkylenephenyl, and NHC0-1 alkylenephenyl;

R3 is, independently if "n" is 2 or more, selected from the group consisting of C1-4 alkyl, such as methyl, OC1-4 alkyl, such as methoxy, halogen, cyano, nitro, C1-4 fluoroalkyl, such as trifluoromethyl;

R10 is hydrogen or C1-4 alkyl, such as methyl or tert-butyl, such as methyl;

the substituent(s) R3 may be connected to any substitutable atom(s) of "Ar";

"n" is an integer from 0 (zero) to 5;

"Ar" is unsubstituted if "n" is 0 (zero); and

"X" is selected from the group consisting of O (oxygen), NH, N-phenyl, N-benzyl, and N—C1-8 alkyl.

Similar to compounds according to formula (I) and (II), compounds according to formula (V) and (VI), may also be used as end-cappers for polymers. It is however envisaged that the curing temperature of compounds according to formula (V) and (VI) may be lower than the curing temperature of compounds according to formula (I) and (II).

The preparation of compounds according to formula (V) or (VI), are generally based on readily available raw materials, such as trimelletic anhydride and propyne. Typically, trimelletic anhydride is activated by reaction with thionyl chloride to form an acid chloride, which is coupled to or propyne in a palladium catalyzed reaction.

A preferred example of a compound according to formula (VI) is 5-(but-2-ynoyl)isoindoline-1,3-dione, also denoted META (MethylEthynylTrimelleticAnhydride). META has the structure indicated below.

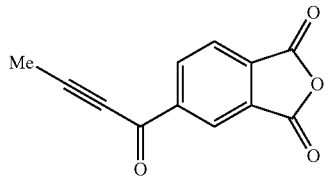 [SMILES: CC#CC(=O)c1ccc2c(c1)C(=O)OC2=O]

In addition to compounds according to formula (I), (II), (V) and (VI), a further embodiment relates to compounds according to formula (VII), (VIII), (IX) and (X)

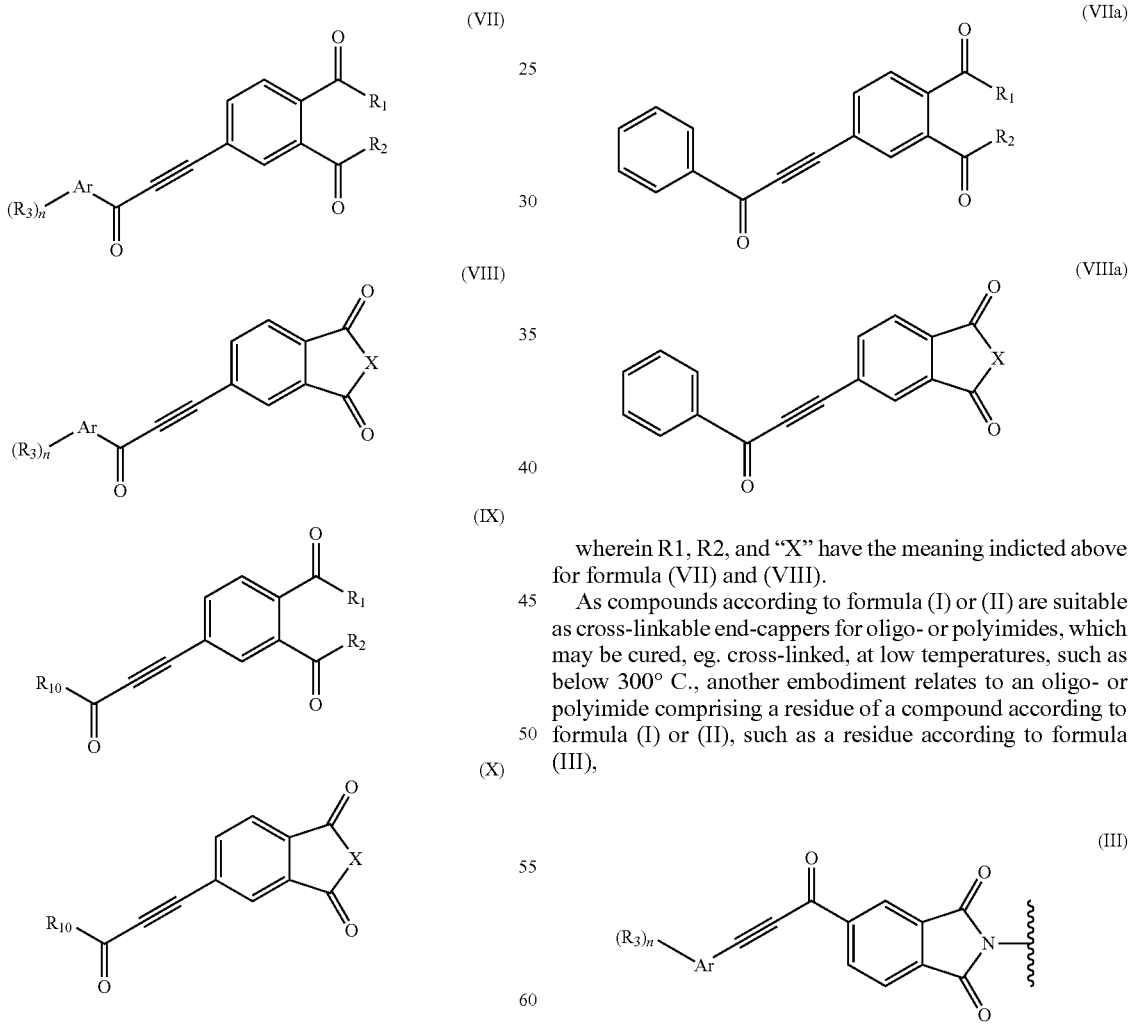

wherein
"Ar" is an aryl, such as phenyl or naphtyl, or a heteroaryl, such as thiophenyl or furanyl;
R1 and R2 are independently selected from the group consisting of OH, halo, such as chloro, OC1-C8 alkyl, such as OC1-C4 alkyl, NH2, NHC1-8 alkyl, N(C1-8 alkyl)$_2$, wherein said alkyl may be the same or different, OC(O)C1-8 alkyl, OC0-1 alkylenephenyl, and NHC0-1 alkylenephenyl;
R3 is, independently if "n" is 2 or more, selected from the group consisting of C1-4 alkyl, such as methyl, OC1-4 alkyl, such as methoxy, halogen, cyano, nitro, C1-4 fluoroalkyl, such as trifluoromethyl;
R10 is hydrogen or C1-4 alkyl, such as methyl or tert-butyl, such as methyl;
the substituent(s) R3 may be connected to any substitutable atom(s) of "Ar";
"n" is an integer from 0 (zero) to 5;
"Ar" is unsubstituted if "n" is 0 (zero); and
"X" is selected from the group consisting of O (oxygen), NH, N-phenyl, N-benzyl, and N—C1-8 alkyl.

Similar to compounds according to formula (I) and (II), compounds according to formula (VII), (VIII), (IX) and (X), may also be used as end-cappers for polymers.

Preferred examples of compounds according to formula (VII) or (VIII) are compounds according to formula (VIIa) or (VIa)

wherein R1, R2, and "X" have the meaning indicted above for formula (VII) and (VIII).

As compounds according to formula (I) or (II) are suitable as cross-linkable end-cappers for oligo- or polyimides, which may be cured, eg. cross-linked, at low temperatures, such as below 300° C., another embodiment relates to an oligo- or polyimide comprising a residue of a compound according to formula (I) or (II), such as a residue according to formula (III), wherein the waved line indicates the point of attachment to the oligo- or polyimide, and "Ar", "n", and R3 have the same meaning as in formula (I) and (II).

The oligo- or polyimide to be end-capped may for example be a an amino terminated oligo- or polyimide, such as an amino terminated oligo- or polyimide obtainable by polymerization of an aromatic dianhydride and an aromatic diamine. A slight excess of the aromatic diamine may be used. Further, the oligo- or polyimide end-capped with a compound according to formula (I) or (II), eg. an oligo- or polyimide comprising oligo- or polyimide comprising a residue according to formula (III), may comprise residues of at least one aromatic dianhydride and at least one aromatic diamine.

According to an embodiment, the aromatic dianhydride may be pyromellitic dianhydride or a dianhydride according to the general formula (XX),

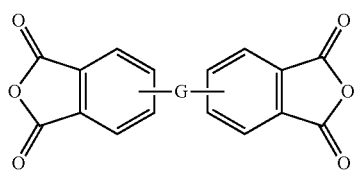

wherein "G" represents a direct bond or a di-valent group selected from the group consisting of a carbonyl group, a methylene group, a sulfone group, a sulfide group, an ether group, an —C(O)-phenylene-C(O)— group, an isopropylidene group, a hexafluoroisopropylidene group, a 3-oxyphenoxy group, a 4-oxyphenoxy group, a 4'-oxy-4-biphenoxy group, and a 4-[1-(4-oxyphenyl)-1-methylethyl]phenoxy group; and wherein "G" may be connected to the 4- or 5-position and the 4'- or the 5'-position, respectively, in the isobenzofuran-1,3-dione residues.

Symmetric aromatic dianhydrides as well asymmetric aromatic dianhydrides are equally possible.

Preferred examples of the aromatic dianhydrides comprise pyromellitic dianhydride, 4,4'-oxydiphthalic anhydride, 2,2-bis-[4-(3,4-dicarboxyphenoxy)phenyl]-propane dianhydride, 3,3',4,4'-benzophenonetetracarboxylic acid dianhydride, 3,3',4,4'-tetracarboxybiphenyl dianhydride, 4,4',5,5'-sulfonyldiphthalic anhydride, and 5,5'-(perfluoropropane-2,2-diyl)bis(isobenzofuran-1,3-dione).

According to an embodiment, the aromatic diamine may be 1,4-diaminobenzene, 1,3-diaminobenzene, or a diamine according to the general formula (XXI)

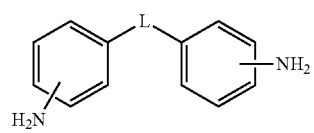

wherein the amino groups may be connected to any substitutable carbon atom in the benzene residues, i.e. to the 2-, 3- or 4-position, and the 2', 3', or 4'-position, respectively; and "L" is a direct bond or a moiety selected from the group consisting of —O—, —S—, —C(O)—, —C(CH$_3$)$_2$—, —C(CF$_3$)$_2$—, —CH$_2$—, 3-oxyphenoxy group, 4-oxyphenoxy group, 4'-oxy-4-biphenoxy group, and 4-[1-(4-oxyphenyl)-1-methylethyl]phenoxy group.

Preferably, the amino groups are connected to the 3- or 4-position of the respective benzene residues. Symmetric di-amines, eg. 3,3'- and 4,4'-substituted di-amines according to general formula (XXI), as well as asymmetric di-amines, eg. 3,4'-, or 4,3'-substituted di-amines according to general formula (XXI), are equally possible.

As well known in the art, asymmetric aromatic diamines and dianhydrides may be used to prepare polyimides with a bent and rotationally hindered structure resulting in high Tg but also in improved processability and high melt fluidity along with and solubility of the resin in organic solvent.

Examples of preferred aromatic diamines comprise 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline, or 3,4'-oxydianiline.

According to an embodiment, the aromatic dianhydride may be pyromellitic dianhydride or 5,5'-(perfluoropropane-2,2-diyl)bis(isobenzofuran-1,3-dione) and the aromatic diamine may be 4,4'-oxydianiline, 1,4-diaminobenzene, or 1,3-diaminobenzene.

An oligo- or polyimide comprising a residue according to formula (III), may, according to an embodiment, have a number average molecular weight of about 1,000 to 20,000, such as from about 2,500 to 10,000. The number average molecular weight, as well as the weight average molecular weight, may be determined with gel permeation chromatography (GPC) or size exclusion chromatography (SEC), by use a of a combination multi-angle light scattering (MALS) detection and refractive index (RI) detection.

An oligoimide comprising a residue according to formula (III), may, according to one embodiment, have a weight average molecular weight of about 1,000 to 10,000, such as from about 2,500 to 7,5000. Further, a polyimide comprising a residue according to formula (III) may, according to one embodiment, have a weight average molecular weight of about 1,000 to 200,000, such as from about 25,000 to 100,000.

As an example, an oligo- or polyimide comprising a residue according to formula (III) and having low molecular weight, eg. comprising less than 20 di-amine residues, may comprise, such as consist of:
one or two residue(s) according to formula (III);
at least one but less than twenty residues of an aromatic diamine; and
at least one but less than twenty residues of an aromatic dianhydride.

As a further example, an oligo- or polyimide comprising a residue according to formula (III) and having intermediate molecular weight, eg. comprising 20 or more diamine residues, but less than 200 diamine residues, may comprise, such as consist of:
one or two residue(s) according to formula (III);
at least 20 but less than 200 residues of an aromatic diamine; and
at least 20 but less than 200 residues of an aromatic dianhydride.

As an additional example, an oligo- or polyimide comprising a residue according to formula (III) and having high molecular weight, eg. comprising at least 200 diamine residues, may comprise, such as consist of:
one or two residue(s) according to formula (III);
at least 200 residues of an aromatic diamine; and
at least 200 residues of an aromatic dianhydride.

As well known within the art, the preparation of oligo- and polyimides are preferably performed in, but not limited to, aprotic solvents, such as dimethylacetamide, dimethylformaide or N-Methylpyrrolidone. Further examples of solvents and mixtures of solvents used in the preparation of oligo- and polyimides are cresol, cresol/toluene, N-Methylpyrrolidone/orto-dichlorobenzene, benzoic acid, and nitrobenzene. Such solvents may be used to obtain oligo- and polyimides comprising PEPA and EBPA residues as well.

Even further examples of solvents include:
Phenol solvents, such as phenol, o-chlorophenol, m-chlorophenol, p-chlorophenol, o-cresol, m-cresol, p-cresol, 2,3-xylenol, 2,4-xylenol, 2,5-xylenol, 2,6-xylenol, 3,4-xylenol, and 3,5-xylenol;
Aprotonic amide solvents, such as N,N-dimethylformamide, N,N-dimethylacetamide, N,N-diethylacetamide, N-methyl-2-pyrrolidone, 1,3-dimethyl-2-imidazolidine, N-methylcaprolactam, and hexamethylphosphorotriamide;
Ether solvents, such as 1,2-dimethoxyethane, bis(2-methoxyethyl) ether, 1,2-bis(2-methoxyethoxy)ethane, tetrahydrofuran, bis[2-(2-methoxyethoxy)ethyl]ether, 1,4-dioxane, and diphenyl ether;
Amine solvents, such as pyridine, quinoline, isoquinoline, alpha-picoline, beta-picoline, gamma-picoline, isophorone, piperidine, 2,4-lutidine, 2,6-lutidine, trimethylamine, triethylamine, tripropylamine, and tributylamine; as well as
Other solvents, such as dimethyl sulfoxide, dimethyl sulfone, sulphorane, diphenyl sulfone, tetramethylurea, anisole, and water.

Typically, oligo- and polyimides are prepared at a dry weight of the monomers corresponding to about 10 to 40 wt %.

In the preparation of oligo- and polyimides, the monomers are mixed at ambient or at slightly elevated temperature, typically from about 25° C. to 50° C., to obtain an oligo- or a polyamic acid as intermediate. Then, the oligo- or polyamic acid intermediate is imidized at a much higher temperature, such as about 180° C., by dehydration eliminating water.

The dehydration, may also be chemical driven, such as by addition if acetic anhydride, whereby by the imidization may be performed at lower temperature, such as room temperature, i.e. about 20 to 25° C., to about 100 to 150° C. Analogously to PEPA and EPA, compounds according to formula (I) or (II), such as PETA, may be, as readily understood by the skilled artesian, incorporated in different ways into oligo- and polyimides.

As an example, compounds according to formula (I) or (II) may be co-polymerized into the polyimide by addition initially or at an early stage to a reaction mixture comprising an aromatic diamine and aromatic dianhydride monomers to be polymerized. Examples of aromatic diamines and dianhydrides are given above. In such co-polymerization it may be preferred to keep the reaction temperature below 120° C., such as below 100° C. or even below 60° C., in preparing the oligo- or polyamic acid end-capped with a residue of a compound according to formula (I) or (II). As also the carbon-carbon triple bond, being conjugated with a carbonyl, of compounds according to formula (I) or (II) may be may react with amines it may preferred if as many amino groups as possible have reacted with the aromatic dianhydride before the temperature is being increased to initiate the imidization.

As the formation of oligo- and polyimides involves formation of oligo- or polyamic acid intermediates, oligo- or polyamic acid intermediates end-capped with a compound according to formula (I) or (II) as well as oligo- or polyimide end-capped with a compound according to formula (I) or (II), may be isolated.

Compounds of formula (I) or (II) may also be reacted with an amino terminated oligo- or polyamic acid or an amino terminated oligo- or polyimide, respectively, after their preparation.

Various molar ratios of a compound according to formula (I) or (II), an aromatic diamine, and an aromatic dianhydride may be used to obtain oligo- or polyimide end-capped with a compound according to formula (I) or (II). Further, the relative molar amount of the aromatic di-amine and/or the compound according to formula (I) or (II), acting as chain terminator, may be used to control the degree of polymerization.

According to one embodiment, the following relative molar amount of a compound according to formula (I) or (II), an aromatic diamine, and an aromatic dianhydride may be used to obtain oligo- or polyimide end-capped with a compound according to formula (I) or (II):
aromatic diamine(s): 1.01 to 1.2;
aromatic dianhydride(s): 1.0 and
compound(s) according to formula (I) or (II): 0.01 to 0.3

As the oligo- or polyimide is to be end-capped with PETA, it is preferred to employ a slight excess of the diamine compared to the amount of the dianhydride. However, use of slight excess of slight excess of the dianhydride is also possible, although it may result in that mono end-capping becomes favored over di end-capping Examples of molar ratios of monomers which may be used to obtain oligo- or polyimide comprising at least one residue of compound according to formula (I) or (II) with various weight average molecular weights are provided below.

| Polymer Mw | 5,000 n | 10,000 n | 25,000 n |
|---|---|---|---|
| 6FDA | 1.000 | 1.000 | 1.000 |
| ODA | 1.153 | 1.068 | 1.025 |
| PETA | 0.329 | 0.140 | 0.051 |

6FDA = 5,5'-(perfluoropropane-2,2-diyl)bis(isobenzofuran-1,3-dione);
ODA = 4,4'-oxydianiline; and
PETA = 5-(3-phenylprop-2-ynoyl)isobenzofuran-1,3-dione;

Pages 137 to 139 in the dissertation thesis "*Synthesis and characterization of thermosetting polyimide oligomers for microelectronics packaging*" by Debra Lynn Dunson, Virginia Polytechnic Institute and State University, from 2000, provides guidance for calculating the molar ratios if using monomers with other molecular weights. Further, the thesis also provides guidance for obtaining other oligo- and polyimides with other weight average molecular weights. In-addition the thesis provides information relating to the preparation of PEPA end-capped oligo- and polyimides. Similar procedures may be employed to prepare oligo- and polyimides comprising residues of compounds according to formula (I) or (II). Thus, the dissertation thesis "*Synthesis and characterization of thermosetting polyimide oligomers for microelectronics packaging*" by Debra Lynn Dunson, Virginia Polytechnic Institute and State University, from 2000 is incorporated herein by reference.

Rather than adding the compound according to formula (I) or (II), the compound according to formula (I) or (II) may also be added subsequently to the reaction of the aromatic diamine, and the aromatic dianhydride, i.e. compounds according to formula (I) or (II) may be used to end-cap an obtained oligo- or poly(amic acid). Subsequently the end-capped oligo- or poly(amic acid) may be cyclo dehydrated to obtain oligo- or polyimide comprising residues of a compound according to formula (I) or (II).

A further embodiment of the present invention relates to a method of obtaining an oligo- or polyimide end-capped by use of a compound according to formula (I) or (II). In such a method a compound according to formula (I) or (II), an aromatic diamine, and an aromatic dianhydride may be mixed in a solvent. Examples of solvents, aromatic diamines, and aromatic dianhydrides, are provided herein above. The monomers may subsequently be allowed to react for about 1 to 24 hours at a temperature of about 20° C. to 50° C., such as about 25° C. to obtain an oligo- or poly(amic acid) comprising at least one residue of a compound according to formula (I) or (II). The obtained oligo- or poly(amic acid) comprising at least one residue of a compound according to formula (I) or (II) may subsequently be dehydrated to obtain an oligo- or polyimide comprising residue according to formula (III).

As readily known to the skilled artisan, oligo- or poly(amic acids) may be dehydrated in various ways. Similarly, oligo- or poly(amic acid) comprising at least one residue of a compound according to formula (I) or (II) may be dehydrated in various ways, such as by raising the temperature to about 160° C. to 190° C., such as about 180° C. for about 3 to 24 hours subsequently to the initially reaction at 20° C. to 50° C. for about 1 to 24 hours. The obtained oligo- or polyimide comprising at least one residue of a compound according to formula (I) or (II) may then be isolated by removing the solvent.

Further, the imidization may be performed at a somewhat lower temperature, eg. about 120-150° C., if an chemical dehydration agent, such as anhydrides, eg. acetic anhydride, is added. Further, other drying agents, such as orthoesters, eg. triethyl orthoformate, coupling reagents, eg. carbodiimides, such as dicyclohexylcarbodiimide (DCC) and diisopropylcarbodiimide (DIC), may be used as chemical dehydration agents. Coupling reagents on solid support may also be used as chemical dehydration agents.

In addition, the imidization may even take place during moulding, such as compression moulding, of the oligo- or poly(amic acid) comprising at least one residue of a compound according to formula (I) or (II). In compression moulding, the mould is typically heated to temperatures 20-50° C. above the softening point before closing the mould. Subsequently to a heat driven imidization and closing the mould, cross-linking of the obtained oligo- or polyimide comprising at least one residue of a compound according to formula (I) or (II) is performed by raising the temperature further, such as to about e.g. to about or less than 300° C. As already described, an isothermal heat staging process may be used for curing oligo- or polyimide comprising at least one residue of a compound according to formula (I) or (II). Thus, the mould temperature of the mould may be increased step wise. As an example, the following temperature stages may used:

1) 220 to 240° C.;
2) 240 to 250° C., and
3) 280 to 300°.

Further, compounds according to formula (I) or (II) are suitable as end-cappers not only for oligo- and polyimides, but also for other types of oligomers and polymers comprising functional group(s) which may react with carboxylic anhydrides, such as compounds according to formula (II), or carboxylic acids or derivatives thereof, such as compounds according to formula (I). Such functional group(s) may be selected from group consisting of primary amino groups, hydroxy groups and epoxy groups.

Thus, another embodiment relates to an oligo- or polyamide, or an epoxy resin, comprising at least one residue of a compound according to formula (I) or (II) as disclosed herein. Similarly, an embodiment relates to an oligo- or polyamide, or an epoxy resin, obtainable by reacting compound according to formula (I) or (II), as disclosed herein, with an oligo- or polyamide, or an epoxy resin.

An end-capped oligo- or polyamide may accordingly comprise a residue according to formula (III),

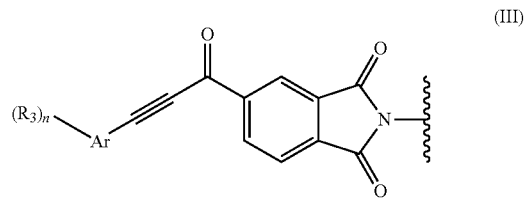

wherein the waved line indicates the point of attachment to the oligo- or polyamide, and "Ar", "n", and R3 have the same meaning as in formula (I) and (II).

As readily known to the skilled artisan, anhydrides may be used to harden epoxy resins. It has been found that compounds according formula (I) or (II), especially compounds according formula (II), may be used to harden epoxy resins. In addition to traditional hardening of the epoxy resins via reaction between the epoxy groups and the anhydride, the epoxy resin end-capped with compounds according formula (I) or (II) may be cured by allowing the ethynyl groups to react, typically by heating the end-capped epoxy resin further. Thus, an en hardened epoxy resin with improved thermal stability and mechanical strength may be obtained. Accordingly, an embodiment relates to the use of compounds according to formula (I) or (II) to harden epoxy resins. In addition to hardening, the hardened epoxy resin may be heat cured, i.e. cross-linked. Further, another embodiment relates to hardened epoxy resin obtainable by hardening with compounds according to formula (I) or (II). An even further embodiment relates to a method of hardening epoxy resin. In such a method, similar to conventional, anhydride based, hardening of epoxy resins, the epoxy resin is mixed with a compound according to formula (I) or (II). Subsequently, the mixture may be heated to promote hardening.

Another embodiment relates to composition comprising an oligo- or polyimide comprising a residue according to formula (III). The composition may further comprise at least one additional polymer, such as at least one non-acetylenical oligo- or polyimide, and/or at least one filler, reinforcement, pigment, plasticizer and/or any other additive known in the art. The oligo- or polyimide comprising a residue according to formula (III) is preferably present in an amount corresponding to at least 10 wt %, such as at least 25, 40, 60, or 80 wt % of the composition. Further, the oligo- or polyimide comprising a residue according to formula (III) may be present in an amount corresponding to not more than 90 wt %, such as not more than 80, 70 or 50 wt %.

Another embodiment relates to an article comprising an oligo- or polyimide comprising a residue according to formula (III), or an epoxy resin hardened by use of a compound according to formula (I) or (II). Optionally, the oligo- or polyimide, or the epoxy resin, in the article has been cross-linked by heating it. Typically examples of articles, comprising an oligo- or polyimide comprising a residue according to formula (III), include flexible films for electronics, wire isolation, wire coatings, wire enamels, ink, and load-bearing structural components.

Similar to PEPA and EPA, also compounds according to formula (I) or (II), as well as compounds comprising a residue of such a compound, may cross-linked by heating them. Without being bound to any theory, it is believed that, upon heating of mixtures of compounds comprising ethynyl moieties, these moieties will eventually start to react. Reaction of two ethynyl moieties of separate molecules will provide a chain extended product, while reaction of three ethynyl moieties of separate molecules is thought to provide a benzene moiety with three "arms". Subsequently, two or three ethynyl moieties present on such "arms" may react to form a cross-linked product. Chain extension, but especially cross-linking, will improve the properties of an oligo- or polymer comprising ethynyl moieties, as has been shown in the art. Heat initiated chain extension, but especially cross-linking, of oligo- or polymers comprising ethynyl moieties is often referred to as curing.

The curing of compounds, such as oligo- or polyimide, comprising a residue according to formula (III), and compositions or articles comprising an oligo- or polyimide comprising a residue according to formula (III), may be accomplished by heating.

Such heating may be performed in an isothermal staging process. As an example, such an isothermal staging process may start by heating the material to be cured to 180° C. to 220° C., such as to about 200° C., for some time, typically 1 to 2 hours. However, also less time, such as less than 1 hour, or less than 30 minutes, may be used. Further, also longer times, such as up to 10 hours may be used. Subsequently, the temperature may be increased in steps. Each step may correspond to an increase of the temperature of 10° C. to 50° C. Further, each step may have a duration of 30 minutes to 10 hours, such as 1 to 2 hours. The last step may be curing at a temperature of 270 to 300° C., such as at about 300° C. In an isothermal staging process the duration of each isothermal step may decrease as the temperature increases. By employing an isothermal staging process curing may be promoted over degradation, especially if the time of each step is decreased as the temperature is increased. A further example of an isothermal staging process, is a process starting at 175° C. in which the temperature is increased by 25° C. every hour until 300° C. is reached.

The curing may also be accomplished by isothermal heating at a temperature of 220° C. to 270° C., such as 230° C. to 250° C. The time of the isothermal heating may be 1 to 24 hours, such as 5 to 15 hours.

The curing may also be a heating process with continuously increasing temperature. Preferably, the heating rate is slow initially but gradually increased as the temperature increases.

A curing cycle for oligo- or polyimide comprising a residue according to formula (III) may in addition to a curing stage also encompass a pre-curing stage and/or a post-curing stage.

Once the resin, eg. an oligo- or polyimide comprising a residue according to formula (III), has been prepared it may be transferred onto fiber, cut or printed into a film. A pre-cure step may be used. In such a step the dry-content may be increased. Further, it may also commence to molecular growth. The temperature during this step may from 50 to 250° C., such as from 180 to 230° C. The duration may be from minutes to hours, depending on system and desired properties. Subsequently, the cure may be performed at a temperature of 230° C. to 250° C. The duration of the curing step may be 1 to 4 hours. Post curing may then optionally be performed to further advance material properties.

Further, alternative curing of compounds, such as an oligo- or polyimide, comprising a residue according to formula (III), or compositions, or articles, comprising a compound comprising a residue according to formula (III), may also be used. Such alternative curing may be accomplished by addition of compounds having at least two amino groups, such as diamines or triamines, to compounds comprising a residue according to formula (III) and heating the compounds. The amino groups of such compounds may react with the carbon-carbon triple bond present in the residue according to formula (III) and thereby connecting compounds comprising residues according to formula (III) to each other by accomplishing chain elongation.

The reactivity of compounds according to formula (I) or (II), which are suitable for end-capping of amine terminated oligo- and polyimides, may be altered by reaction with compounds, such as aminofenols or aminoresorcinols, O-acetylated aminofenols or O-acetylated aminoresorcinols, aminobenzoic or aminophthalic acids or esters. Thus, compounds according to formula (I) or (II) may also be used to obtain cross-linkers for polyetherketones, polycarbonates etc.

According to an embodiment, examples of such compounds with altered reactivity are compounds according to formula (XV) and (XVI)

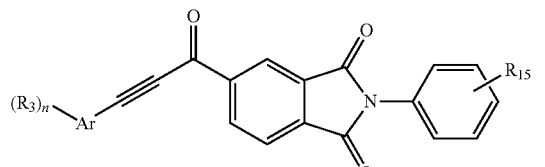

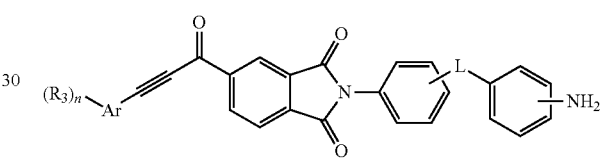

wherein
"Ar", "n", and R3 have the same meaning as in formula (I) and (II);
"L" has the same meaning as in formula (XXI);
R15 is OH, NH2, COOH, C(O)OC1-8 alkyl, or C(O)Cl, and is connected to any substitutable carbon atom of the indicated benzene residue of formula (XV);
"L" and the NH2 group of formula (XVI), respectively, may be connected to any substitutable carbon atoms of the respective indicated benzene residue of formula (XVI).

It is to be noted that R1 and R2 of formula (I) and "X" of formula (II) also may represent more intricate groups. Thus, an embodiment relates to derivatives of compounds according to formula (I) or (II). Especially, such derivatives may be compounds comprising a residue according to formula (IIIa),

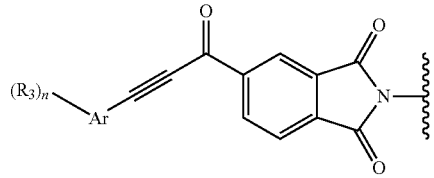

wherein the waved line indicates the point of attachment to the remaining part of the derivative, and "Ar", "n", and R3 have the same meaning as in formula (I) and (II). Such derivatives may be obtained be reacting a compound comprising at least one primary amino group with a compound according to formula (I) or (II). Further, such derivates may comprise at least two residues according to formula (IIIa).

Preferred examples of such derivates comprising at least two residues according to formula (IIIa), are derivatives further comprising at least one residue of an aromatic diamine, such as 1,3- or 1,4-diaminobenzene. Further, examples of aromatic diamines 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline, 4,4'-diaminodiphenyl sulfone and 3,4'-oxydianiline.

According to an embodiment, derivatives comprising at least two residues according to formula (IIIa) may be derivatives according to formula (IIIb)

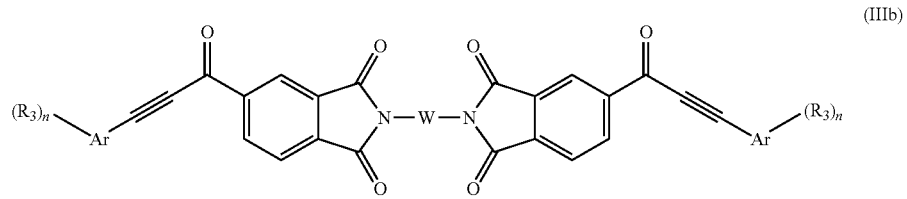

(IIIb)

wherein

"Ar", "n", and R3 have the same meaning as in formula (I) and (II); and

"W" is a radical selected from the group consisting of:

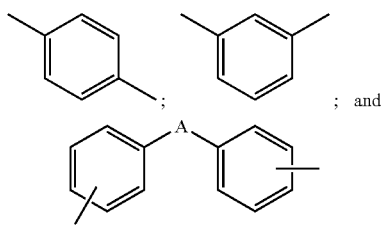

; and wherein "A" is a direct bond or a moiety selected from the group consisting of —O—, —S—, —C(O)—, —C(CH3)2-, —C(CF3)2-, —CH2-, 3-oxyphenoxy group, 4-oxyphenoxy group, 4'-oxy-4-biphenoxy group, and 4-[1-(4-oxyphenyl)-1-methylethyl]phenoxy group. In derivatives according to formula (IIIb), the radicals according to formula (IIIa) may be connected to any carbon atoms in the benzene residues of "W", i.e. to the 2-, 3- or 4-position, and the 2', 3', or 4'-position, respectively. Symmetric derivatives, eg. 4,4'-derivatives, and asymmetric derivatives, eg. 3,4'-derivatives, are equally possible.

Derivatives according to formula (IIIb) may be used as additives to oligo- or polyimides end-capped with a compound according to formula (I) or (II), whereby the cross-linking density may be increased. Further, derivatives according to formula (IIIb) may be used as additives to oligo- or polyimide, whereby interpenetrating networks may be obtained upon curing of the derivatives.

Thus, a further embodiment relates to a composition comprising a derivative according to formula (IIIb), and an oligo- or polyimide comprising a residue according to formula (III) and/or a non-acetylenical oligo- or polyimide. Such a composition may comprise 1 to 20 wt % of a derivative according to formula (IIIb). As a derivative according to formula (IIIb) may act as a curable resin, even higher amounts may be used. Thus, the amount of the derivative according to formula (IIIb) in the composition may, according to an embodiment, be 20 to 100 wt %, such as 25 to 75 wt %.

As elaborated below, PETA may be synthesized from trimellitic anhydride and ethynylbensen, which both are readily available. Trimelletic anhydride may be obtained from pseudocumene (1,2,4-trimethylbenzene), while ethynylbenzene may be obtained from styrene or bromobenzene. Thus, PETA may be produced in large quantities, which is prerequisite to find use a cross-linker within the polymer industry. Further, the availability of suitable starting materials also means that price may be kept at a moderate level.

A further embodiment relates to a method of producing a monomer according to formula (II) as disclosed herein. Such a method comprises the step of:

reacting trimelletic anhydride or a derivative thereof, such as trimellitic anhydride chloride, with a compound according to formula (IV) to obtain a monomer according to formula (II).

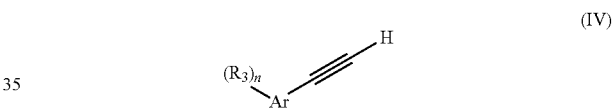

(IV)

wherein "Ar", R3 and "n" have the meaning indicated above for formula (I) and (II). Further, the method may optionally also include the step of purifying the obtained compound according to formula (II).

The reaction between the trimellitic anhydride or the derivative thereof and the compound according to formula (IV) may typically be a palladium catalyzed coupling reaction, such as a Sonagashira coupling.

According to one embodiment, the reaction may thus be performed in the presence of a compound comprising palladium, such as Bis(triphenylphosphine)palladiumchloride, and a compound comprising cupper, such as CuI. A phosphine, such as tri-phenylphsophine, may be also added to the reaction mixture.

Further, the crude product may be purified via standard techniques, such as chromatography or re-crystallization. Chromatography may typically be normal phase chromatography on silica. Re-crystallization may be performed in solvents such as, aromatic hydrocarbons, optionally with the addition of carboxylic acids, such as formic or acetic acid.

According to an embodiment, compounds according to formula (II), such as a compound obtained via the method above, may be purified by normal phase chromatography on silica using an organic solvent or a mixture of organic solvents, such as heptane/ethyl acetate. As compounds according to formula (II) to some extent may react with the silica, purification by normal phase chromatography is a less preferred purification method. If using normal phase chromatography it is preferred to employ a short colon, i.e. to filter rather than chromatograph the product through silica.

According to another embodiment, compounds according to formula (II), such as compound obtained via the method above, may be purified by re-crystallization in solvents, such as aromatic hydrocarbons, eg. toluene or xylene. In such re-crystallization, the yield may be increased by addition of carboxylic acids, such as formic or acetic acid. Re-crystallization is a preferred method of purification.

Without further elaboration, it is believed that one skilled in the art can, using the preceding description, utilize the present invention to its fullest extent. The preferred specific embodiments described herein are, therefore, to be construed as merely illustrative and not limitative of the remainder of the description in any way whatsoever. Further, although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do not preclude a plurality.

EXPERIMENTAL

Figure 1:
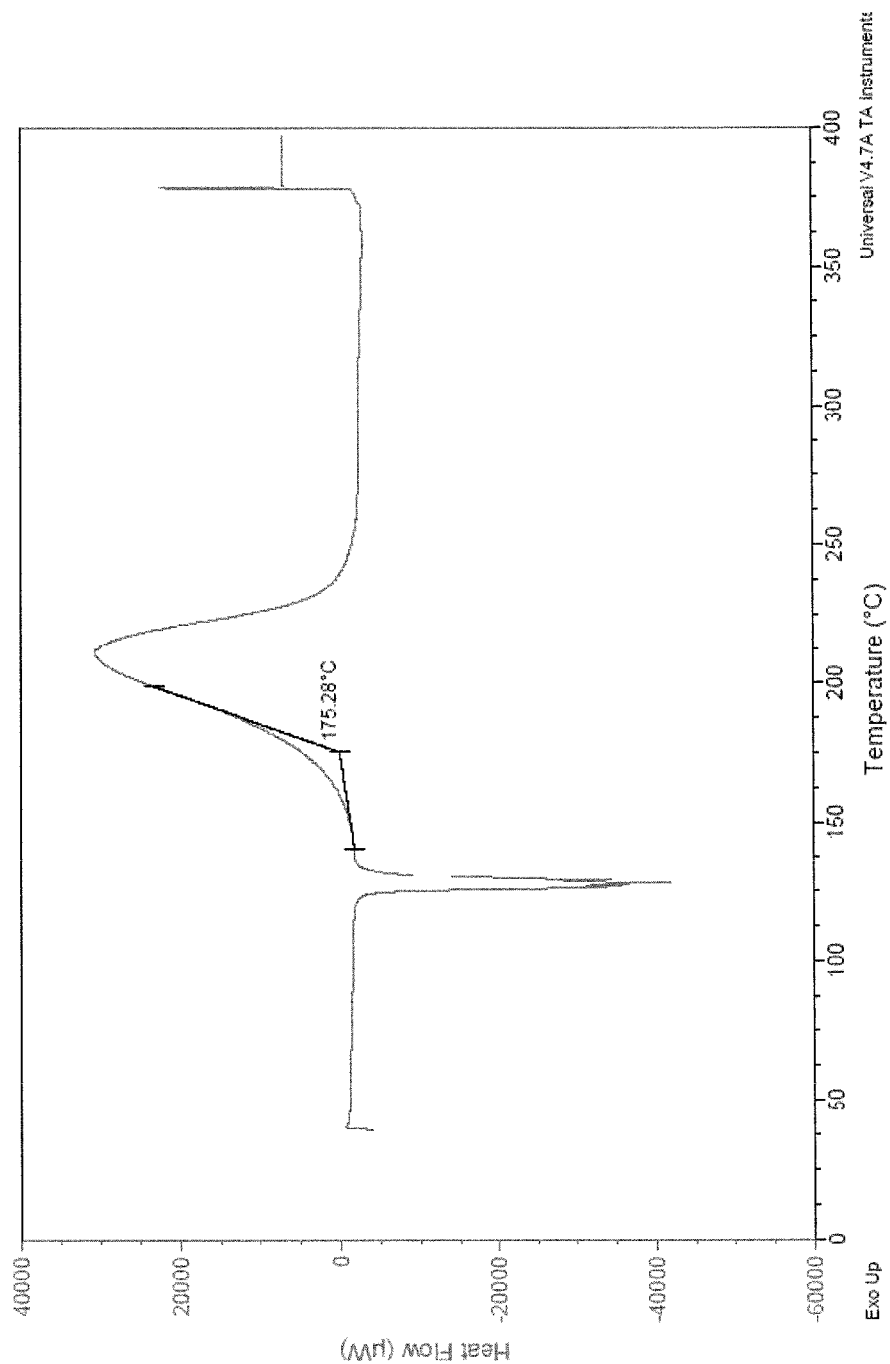
FIG. 1 depicts a DSC-thermogram for EPA.

The following examples are mere examples and should by no mean be interpreted to limit the scope of the invention. Rather, the invention is limited only by the accompanying claims.

| Abbreviations | |
|---|---|
| PETA | Phenylethynyl trimelletic anhydride (5-(3-phenylprop-2-ynoyl)isobenzofuran-1,3-dione) |
| PEPA | Phenylethynyl phtalic anhydride |
| EPA | Ethynyl phtalic anhydride |
| PD-PETA | 2,2'-(1,4-phenylene)bis(5-(3-phenylpropioloyl)isoindoline-1,3-dione) |
| PETI | Phenyl ethynyl terminated imide oligomer |
| BPDA | 3,3',4,4'-Biphenyl tetracarboxylic dianhydride |
| 4,4-ODA | 4,4'-oxydianiline |
| NMP | N-Methyl-2-pyrrolidone |

5-(3-phenylprop-2-ynoyl)isobenzofuran-1,3-dione (PhenylEthynylTrimelleticAnhydride; PETA)

0.16 g of palladium acetate (0.78 mmol) was added to a mixture of 300 ml toluene, 54.6 ml triethyl amine (0.39 mol), 43 ml phenyl acetylene (0.39 mol) and 75 g of trimellitic anhydride chloride (0.36 mol). The mixture was stirred at rt for 1.5 hours, whereupon 16.5 ml triethyl amine (0.12 mol) was added. The mixture was stirred for additionally 1 hour, whereupon the resulting solid was filtered of. The solid was washed with 150 ml toluene, and then suspended in 750 ml ethyl acetate. The mixture was refluxed for 30 min, whereupon it was filtered on a bed of silica gel. The filtrate was concentrated under vacuum, and the precipitate formed was filtered of, and washed with toluene. The solid was dried under vacuum to give 39 g of PETA (0.14 mol), $^1$H NMR (400 MHz, CDCl$_3$): δ 8.84 (q, 1H, J=1.4 Hz), 8.74 (dd, 1H, J=7.8 Hz), 8.22 (dd, 1H, J=8.0 Hz), 7.77 (m, 1H) 7.59 (m, 2H), 7.51 (m, 2H).

Prior to analysis, the product was hydrolysis in methanol containing 2% sulfuric acid to provide two regio isomers. The regio isomers was analyzed by LC/UV/MS performed on an Agilent 1100 system comprised of a degasser, binary pump, autosampler, single wavelength UV detector, operating at 254 nm, and a single quadrupole mass detector, equipped with an electrospray ionization source, operating in single ion monitoring. The mobile phase was H$_2$O:Methanol (50/50) with 0.1% acetic acid and the separation column (150 mm*2 mm) was packed with octadecyl coated silica particles with an average diameter of 3 μm. The two regio isomers, obtained by the hydrolysis of PETA, had retention factors of 2.64 and 2.93, respectively. Both isomers were found to form ions with m/z's: 277, 309 and 331.

Figure 2:
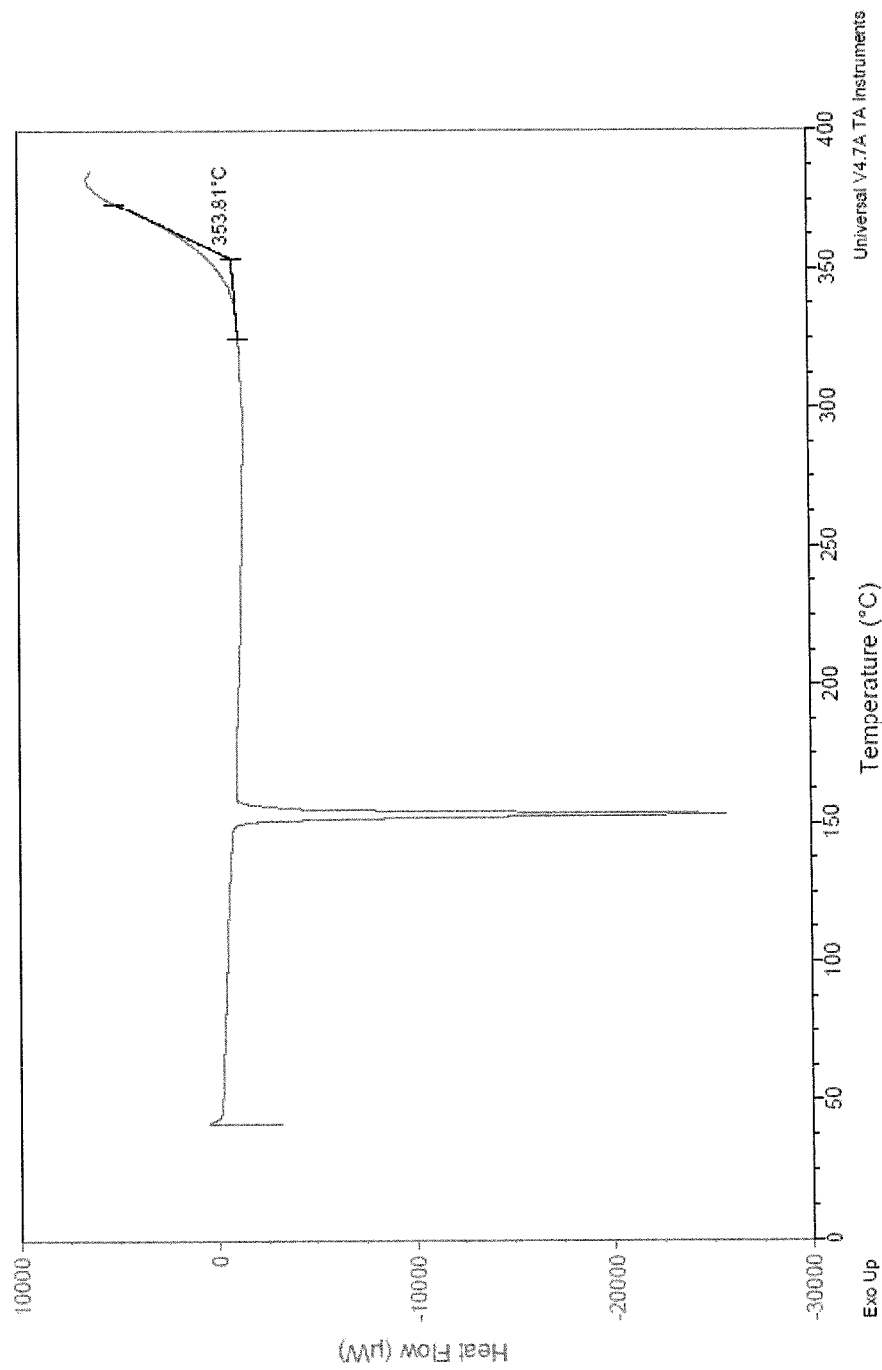
FIG. 2 depicts a DSC-thermogram for PEPA.
Figure 3:
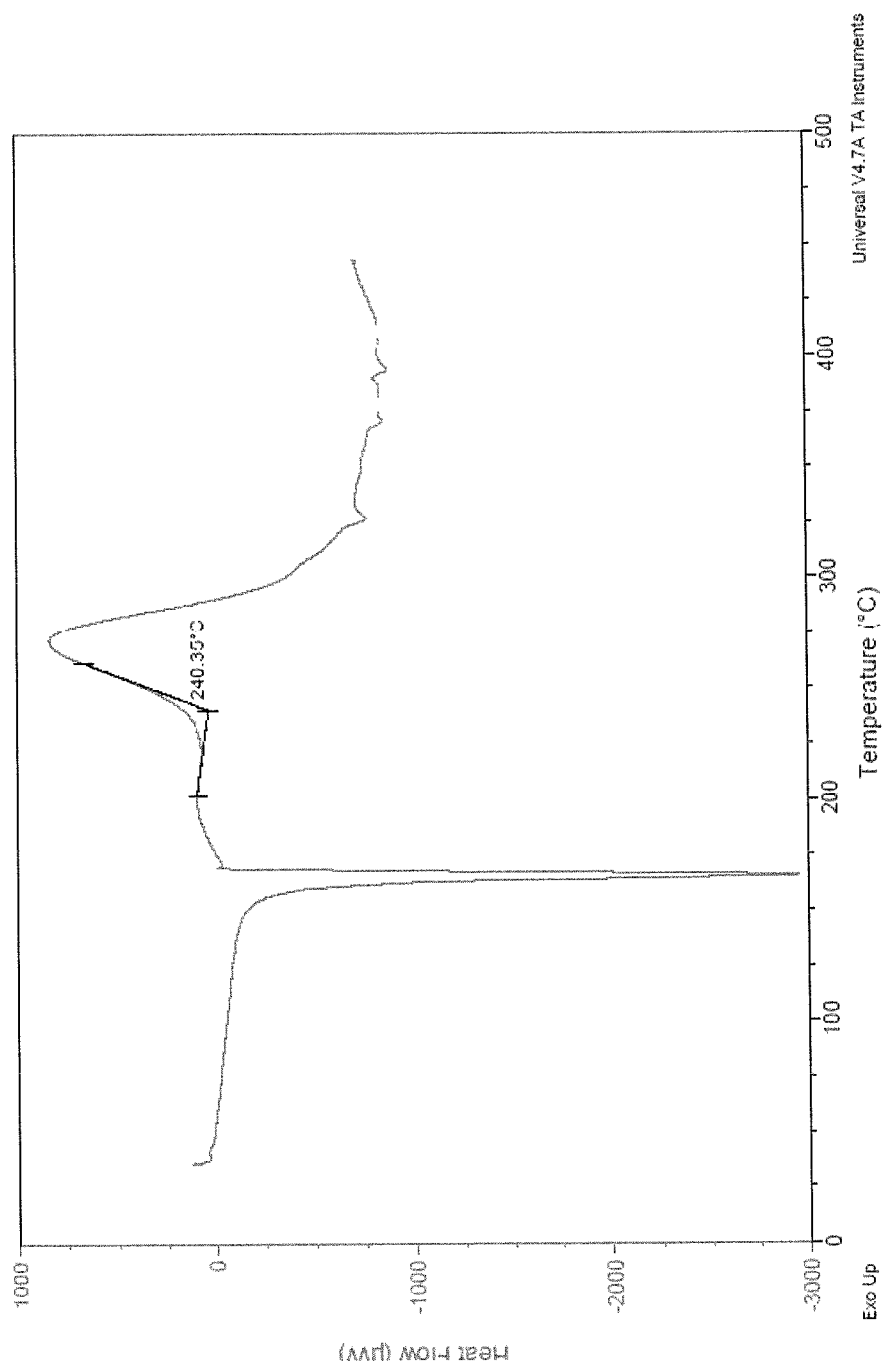
FIG. 3 depicts a DSC-thermogram for PETA.

PETA, as well as PEPA and EPA, were analyzed by differential scanning calorimetry (DSC) using a TA instrument DSC Q2000 with a ramp of 50° C.-400° C. (10°/min). As seen in FIGS. 1 to 3, onset for curing was found to be about 175° C. for EPA, about 240° C. for PETA and about 355° C. for PEPA. This confirms that PETA may be cross-linked at much lower temperatures compared to PEPA. Further, it is noted that while the curing temperature for PEPA and PETI are comparable, this is not the case for EPA.

Polyimid End-Capped with PETA

BPDA (25.0 g, 0.085 mmol), 4,4-ODA (15.3 g, 0.077 mmol), PETA (2.35, 0.0085 mmol) and acetic acid were mixed at room temperature over nitrogen atmosphere and heated to 100° C. for two hours. NMP (350 mL) was added to the reaction mixture and the temperature was raised to 120° C. for one hour during which the color of the reaction mixture turned orange. The temperature was further raised to 145° C., and acetic acid started to distill off from the reactor during 1.5 hours while the temperature was increased to 175° C. The reaction mixture was cooled down to room temperature and water (300 mL) was added. The mixture was filtered, washed with water (600 mL), washed with methanol (300 mL) and dried at 100° C. over vacuum over night to give 33.5 g of a polyimid end-capped with PETA as an yellow solid (79 wt % recovery).

The obtained end-capped polymimid was analyzed by differential scanning calorimetry (DSC) using a TA instrument DSC Q2000. The heating profile employed was: Heat: 35° C.=>390° C. (10°/min); Cool: 390° C.=>70° C. (5° C./min); and Heat: 70° C.=>400° C. (10°/min).

Figure 4:
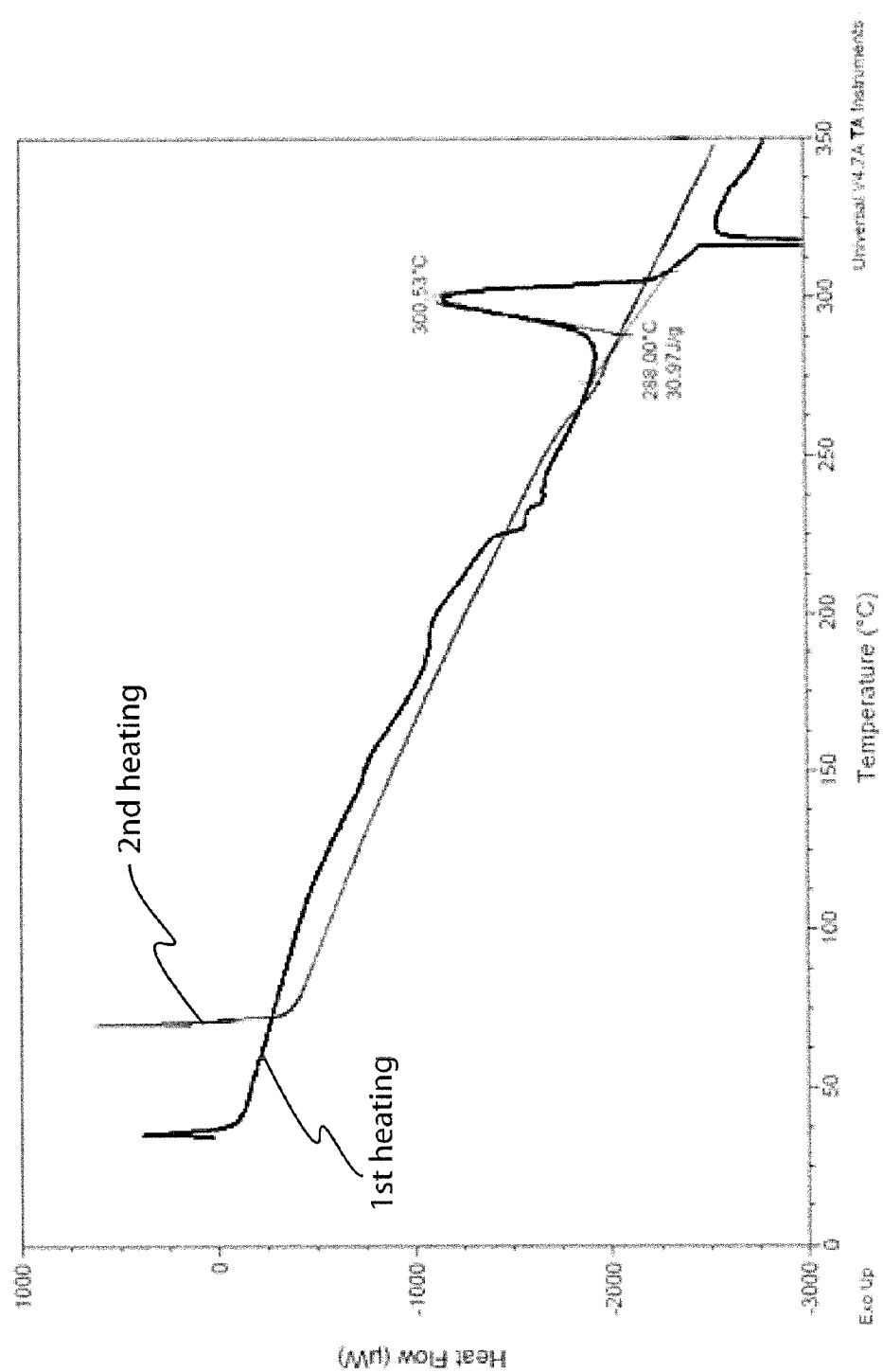
FIG. 4 depicts a DSC-thermogram for a polyimid end-capped with PETA.

The DSC-thermogram (FIG. 4) of the polyimide end-capped with PETA clearly shows a curing exotherm at 270-300° C. in the 1:st heating which is not seen in the second heating, indicating complete cure of the product.

2,2'-(1,3-phenylene)bis(5-(3-phenylpropioloyl)isoindoline-1,3-dione)

5-(3-phenylprop-2-ynoyl)isobenzofuran-1,3-dione (1 mol), m-phenylenediamine (0.53 mol) and acetic acid (2 L) were mixed in a glass reactor and heated to 60° C. over night. The reaction mixture was allowed to cool down to room temperature and precipitation was filtered off. The solid product was washed with heptane (2.5 L). Subsequent to filtering of the washed solid product it was dried to provide m-phenylenediamine end-capped with PETA as a yellowish/brown product (0.3 kg, yield 96%), $^1$H-NMR: (400 MHz d-DMSO): δ 8.72 (dd, 2H, J=8.0, 1.5 Hz), 8.50 (s, 2H) 8.22 (d, 2H, J=7.7 Hz), 7.89 (m, 4H), 7.69-7.57 (m, 10H).

2,2'-(1,3-phenylene)bis(5-(3-phenylpropioloyl)isoindoline-1,3-dione) (PD-PETA) was used as a model system to study the curing behavior of PETA. The curing behavior and the resulting thermal stability were studied by thermo gravimetric analysis (TGA). Samples of PD-PETA (3 to 40 mg) subjected to various heating cycles (data provided below) using a TGA model Q50 from TA instruments. The onset of thermal degradation in the cured PD-PETA, defined as the intercept between the base line and the tangent drawn through the point at the highest slope on the curve, as well as the weight loss at 550° C. were determined and are provided below in Table 1.

TABLE 1

| Curing method | Onset | Weight loss |
|---|---|---|
| 1) 10 hours at 180° C.[1] | 274° C. | 35 wt % |
| 2) 1 hour at 230° C.[2] | 360° C. | 14.4 wt % |
| 3) 1 hours at 250° C.[3] | 370° C. | 13.5 wt % |
| 4) 10 hours at 230° C.[4] | 375° C. | 12.7 wt % |
| 5) Staging from 175 to 300° C. at a rate of 25° C. per hour[5] | >384° C. | 11.3 wt % |

[1]Cycle isothermal 180° C. 10 hours
Method Log:
1: Ramp 20.00° C./min to 180.00° C.
2: Isothermal for 600.00 min
3: Ramp 20.00° C./min to 550.00° C.
4: End of method
[2]Cycle isothermal 230° C. 1 hours
Method Log:
1: Ramp 20.00° C./min to 200.00° C.
2: Isothermal for 20.00 min
3: Ramp 20.00° C./min to 230.00° C.
4: Isothermal for 60.00 min
5: Mark end of cycle 0
6: Ramp 20.00° C./min to 550.00° C.
7: Mark end of cycle 0
8: End of method
[3]Cycle isothermal 250° C. 1 hours
Method Log:
1: Ramp 20.00° C./min to 200.00° C.
2: Isothermal for 20.00 min
3: Ramp 20.00° C./min to 250.00° C.
4: Isothermal for 60.00 min
5: Mark end of cycle 0
6: Ramp 20.00° C./min to 550.00° C.
7: Mark end of cycle 0
8: End of method
[4]Cycle isothermal 230° C. 10 hours
Method Log:
1: Ramp 20.00° C./min to 230.00° C.
2: Isothermal for 600.00 min
3: Ramp 20.00° C./min to 550.00° C.
4: End of method
[5]Staging 1 hour @ 175° C.-300° C. (25° C. increment/stage)
Method Log:
1: Ramp 20.00° C./min to 175.00° C.
2: Isothermal for 60.00 min
3: Mark end of cycle 0
4: Ramp 20.00° C./min to 200.00° C.
5: Isothermal for 60.00 min
6: Mark end of cycle 0
7: Ramp 20.00° C./min to 225.00° C.
8: Isothermal for 60.00 min
9: Mark end of cycle 0
10: Ramp 20.00° C./min to 250.00° C.
11: Isothermal for 60.00 min
12: Mark end of cycle 0
13: Ramp 20.00° C./min to 275.00° C.
14: Isothermal for 60.00 min
15: Mark end of cycle 0
16: Ramp 20.00° C./min to 300.00° C.
17: Isothermal for 60.00 min
18: Mark end of cycle 0
19: Ramp 20.00° C./min to 550.00° C.
20: Mark end of cycle 0
21: End of method As is apparent from table 1, a higher temperature than 180° C. seems to be required to efficiently cure PD-PETA. Further, good thermal stability seems to be obtained via an isothermal staged curing process.

The invention claimed is:

1. A compound according to formula (I) or (II),

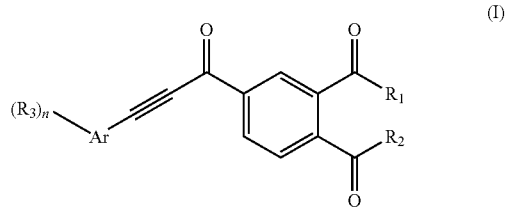

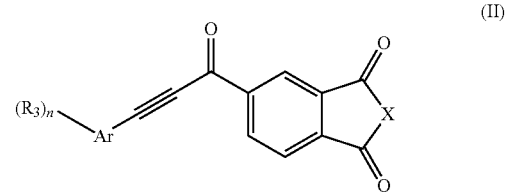

wherein

"Ar" is an aryl or a heteroaryl;

R1 and R2 are independently selected from the group consisting of OH, halogen, OC1-C8 alkyl, NH2, NHC1-8 alkyl, N(C1-8 alkyl)$_2$, wherein said alkyl may be the same or different, OC(O)C1-8 alkyl, O(methylenephenyl), O-phenyl, and NH-phenyl and NH(methylenephenyl);

R3 is independently selected from the group consisting of C1-4 alkyl, OC1-4 alkyl, halogen, cyano, nitro, C1-4 fluoroalkyl;

the substituent(s) R3 may be connected to any substitutable atom(s) of "Ar";

"n" is an integer from 0 (zero) to 5; and

"X" is selected from the group consisting of O (oxygen), NH, N-phenyl, N-benzyl, and N—C1-8 alkyl.

2. The compound according to claim 1, wherein "Ar" is phenyl, naphtyl, thiophenyl or furanyl.

3. The compound according to claim 1, wherein "Ar" is phenyl.

4. The compound according to claim 1, wherein the integer "n" is 0; or wherein "n" is 1 or more, and R3 is independently selected from the group consisting of methyl, methoxy, nitro, and trifluoromethyl.

5. The compound according to claim 1, wherein said compound is a compound according to formula (II) and "X" is O (oxygen); or wherein said compound is a compound according to formula (I) and R1 and R2 are selected from OH, chloro, and OC1-C8 alkyl.

6. The compound according to claim 5, wherein said compound is

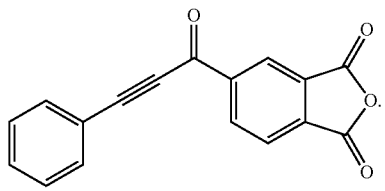

7. An oligo- or polyimide comprising a residue according to formula (III),

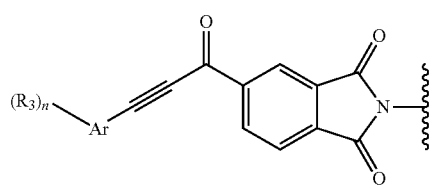
(III)

wherein the waved line indicates the point of attachment to the oligo- or polyimide;

"Ar" is an aryl or a heteroaryl;

"n" is an integer from 0 (zero) to 5;

R3 is independently selected from the group consisting of C1-4 alkyl, OC1-4 alkyl, halogen, cyano, nitro, C1-4 fluoroalkyl; and the substituent(s) R3 may be connected to any substitutable atom(s) of "Ar".

8. The oligo- or polyimide according to claim 7, wherein said oligo- or polyimide comprises at least one residue of an aromatic dianhydride selected from the group consisting of pyromellitic dianhydride, 4,4'-oxydiphthalic anhydride, 2,2-bis-[4-(3,4-dicarboxyphenoxy)phenyl]-propane dianhydride, 3,3',4,4'-benzophenonetetracarboxylic acid dianhydride, 3,3',4,4'-tetracarboxybiphenyl dianhydride, 4,4',5,5'-sulfonyldiphthalic anhydride, and 5,5'-(perfluoropropane-2,2-diyl)bis(isobenzofuran-1,3-dione); and at least one residue of an aromatic diamine selected from the group consisting of 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline, and 3,4'-oxydianiline.

9. The oligo- or polyimide according to claim 7, having a number average molecular weight of about 1,000 to 20,000; or having a weight average molecular weight of about 1,000 to 200,000.

10. A composition comprising an oligo- or polyimide according to claim 7, and an additional polymer, at least one filler, reinforcement, pigment, and/or plasticizer; wherein the oligo- or polyimide is present in an amount corresponding to at least 10 wt % and/or in an amount corresponding to not more than 90 wt %.

11. A method of producing a compound according to formula (II) according to claim 1, wherein X" is O (oxygen), the method comprising the step of:

reacting trimellitic anhydride chloride with a compound according to formula (IV)

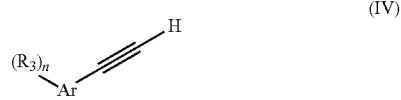
(IV)

wherein "Ar" is an aryl or a heteroaryl;

"n" is an integer from 0 (zero) to 5; and

R3 is independently selected from the group consisting of C1-4 alkyl, OC1-4 alkyl, halogen, cyano, nitro, C1-4 fluoroalkyl.

12. The method according to claim 11, further comprising the step of re-crystallization of the obtained compound according to formula (II) in the presence of acetic acid.

13. An article comprising an oligo- or polyimide according to claim 7, wherein the oligo- or polyimide has been cured by heating it.

14. An oligo- or polyimide, obtainable by co-polymerization of:

a compound according to claim 1;

an aromatic dianhydride selected from the group consisting pyromellitic dianhydride and an aromatic dianhydride according to the general formula (XX),

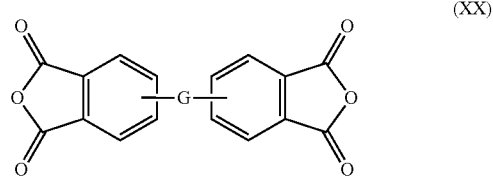
(XX)

wherein "G" represents a direct bond or a di-valent group selected from the group consisting of a carbonyl group, a methylene group, a sulfone group, a sulfide group, an ether group, an —C(O)-phenylene-C(O)— group, an isopropylidene group, a hexafluoroisopropylidene group, a 3-oxyphenoxy group, a 4-oxyphenoxy group, a 4'-oxy-4-biphenoxy group, and a 4-[1-(4-oxyphenyl)-1-methylethyl]phenoxy group; and wherein "G" is connected to the 4- or 5-position and the 4'- or the 5'-position, respectively, in the isobenzofuran-1,3-dione residues; and an aromatic diamine selected from the group consisting of 1,4-diaminobenzene, 1,3-diaminobenzene, and an aromatic diamine according to the general formula (XXI)

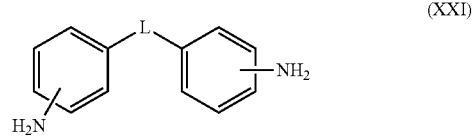
(XXI)

wherein the amino groups may be connected to any substitutable carbon atom in the benzene residues; and "L" is a direct bond or a moiety selected from the group consisting of —O—, —S—, —C(O)—, —C(CH$_3$)$_2$—, —(CF$_3$)$_2$—, —CH$_2$—, 3-oxyphenoxy group, 4-oxyphenoxy group, 4'-oxy-4-biphenoxy group, and 4-[1-(4-oxyphenyl)-1-methylethyl]phenoxy group.

15. The oligo- or polyimide according to claim 14, wherein said aromatic dianhydride is selected from the group consisting of pyromellitic dianhydride, 4,4'-oxydiphthalic anhydride, 2,2-bis-[4-(3,4-dicarboxyphenoxy)phenyl]-propane dianhydride, 3,3',4,4'-benzophenonetetracarboxylic acid dianhydride, 3,3',4,4'-tetracarboxybiphenyl dianhydride, 4,4',5,5'-sulfonyldiphthalic anhydride, and 5,5'-(perfluoropropane-2,2-diyl)bis(isobenzofuran-1,3-dione); and
said aromatic di-amine is selected from the group consisting of 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline, and 3,4'-oxydianiline.

16. A compound according to formula (XV) or (XVI)

(XV)

(XVI)

wherein
"Ar" is an aryl or a heteroaryl;
"n" is an integer from 0 (zero) to 5;
R3 is independently selected from the group consisting of C1-4 alkyl, OC1-4 alkyl, halogen, cyano, nitro, C1-4 fluoroalkyl;
R15 is OH, NH2, COOH, C(O)OC1-8 alkyl, or C(O)Cl, and is connected to any substitutable carbon atom of the indicated benzene residue of formula (XV);
"L" is a direct bond or a moiety selected from the group consisting of —O—, —S—, —C(O)—, —C(CH$_3$)$_2$—, —C(CF$_3$)$_2$—, —CH$_2$—, 3-oxyphenoxy group, 4-oxyphenoxy group, 4'-oxy-4-biphenoxy group, and 4-[1-(4-oxyphenyl)-1-methylethyl]phenoxy group; and
"L" and the NH2 group of formula (XVI), respectively, are connected to any substitutable carbon atoms of the respective indicated benzene residue of formula (XVI).

17. A derivative according to formula (IIIb)

wherein
"Ar" is an aryl or a heteroaryl;
"n" is an integer from 0 (zero) to 5;
R3 is independently selected from the group consisting of C1-4 alkyl, OC1-4 alkyl, halogen, cyano, nitro, C1-4 fluoroalkyl; and
"W" is a radical selected from the group consisting of:

wherein "A" is a direct bond or a moiety selected from the group consisting of —O—, —S—, —C(O)—, —C(CH$_3$)2-, —C(CF$_3$)$_2$—, and —CH$_2$.

18. The derivative according to claim 17, wherein "Ar" is phenyl and the integer "n" is 0.

19. A composition comprising a derivative according to claim 17, and an oligo- or polyimide comprising a residue according to formula (III), (III)

wherein the waved line indicates the point of attachment to the oligo- or polyimide, and "Ar" is an aryl or a heteroaryl, "n" is an integer from 0 (zero) to 5, and R3 is independently selected from the group consisting of C1-4 alkyl, OC1-4 alkyl, halogen, cyano, nitro, C1-4 fluoroalkyl, and/or a non-acetylenical oligo- or polyimide.

20. A composition comprising a derivative according to claim 17, and an oligo- or polyimide obtainable by co-polymerization of:
a compound according to formula (I) or (II), (IIIb)

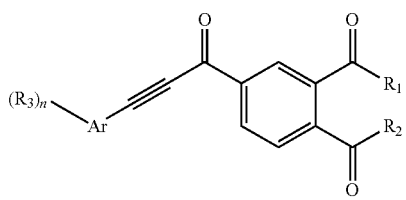

(I)

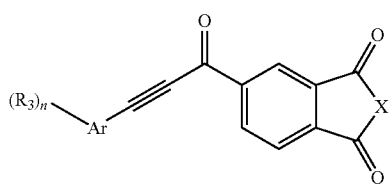

(II)

wherein

"Ar" is an aryl or a heteroaryl;

R1 and R2 are independently selected from the group consisting of OH, halogen, OC1-C8 alkyl, NH2, NHC1-8 alkyl, N(C1-8 alkyl)$_2$, wherein said alkyl may be the same or different, OC(O)C1-8 alkyl, O(methylenephenyl), O-phenyl, and NH-phenyl and NH(methylenephenyl);

R3 is independently selected from the group consisting of C1-4 alkyl, OC1-4 alkyl, halogen, cyano, nitro, C1-4 fluoroalkyl;

the substituent(s) R3 may be connected to any substitutable atom(s) of "Ar";

"n" is an integer from 0 (zero) to 5; and

"X" is selected from the group consisting of O (oxygen), NH, N-phenyl, N-benzyl, and N—C1-8 alkyl; and an aromatic dianhydride selected from the group consisting pyromellitic dianhydride and an aromatic dianhydride according to the general formula (XX),

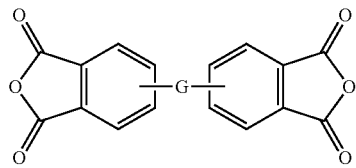

(XX)

wherein "G" represents a direct bond or a di-valent group selected from the group consisting of a carbonyl group, a methylene group, a sulfone group, a sulfide group, an ether group, an —C(O)-phenylene-C(O)— group, an isopropylidene group, a hexafluoroisopropylidene group, a 3-oxyphenoxy group, a 4-oxyphenoxy group, a 4'-oxy-4-biphenoxy group, and a 4-[1-(4-oxyphenyl)-1-methylethyl]phenoxy group; and wherein "G" is connected to the 4- or 5-position and the 4'- or the 5'-position, respectively, in the isobenzofuran-1,3-dione residues; and an aromatic diamine selected from the group consisting of 1,4-diaminobenzene, 1,3-diaminobenzene, and an aromatic diamine according to the general formula (XXI)

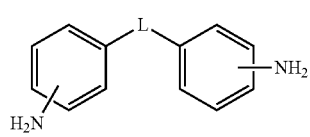

(XXI)

wherein the amino groups may be connected to any substitutable carbon atom in the benzene residues; and "L" is a direct bond or a moiety selected from the group consisting of —O—, —S—, —C(O)—, —C(CH$_3$)$_2$—, —C(CF$_3$)$_2$—, —CH$_2$—, 3-oxyphenoxy group, 4-oxyphenoxy group, 4'-oxy-4-biphenoxy group, and 4-[1-(4-oxyphenyl)-1-methylethyl]phenoxy group;

and/or a non-acetylenical oligo- or polyimide.

* * * * *